(12) United States Patent
Toyoda

(10) Patent No.: US 10,067,073 B2
(45) Date of Patent: Sep. 4, 2018

(54) METHOD OF MANUFACTURING PRINTED CIRCUIT BOARD AND METHOD OF INSPECTING PRINTED CIRCUIT BOARD

(71) Applicant: Nitto Denko Corporation, Ibaraki-shi, Osaka (JP)

(72) Inventor: Yoshihiro Toyoda, Ibaraki (JP)

(73) Assignee: NITTO DENKO CORPORATION, Osaka (JP)

(*) Notice: Subject to any disclaimer, the term of this patent is extended or adjusted under 35 U.S.C. 154(b) by 387 days.

(21) Appl. No.: 15/057,621

(22) Filed: Mar. 1, 2016

(65) Prior Publication Data
US 2016/0266050 A1    Sep. 15, 2016

(30) Foreign Application Priority Data

Mar. 12, 2015 (JP) ................................ 2015-049788

(51) Int. Cl.
*G01N 21/956* (2006.01)
*G01N 21/88* (2006.01)
(Continued)

(52) U.S. Cl.
CPC ....... *G01N 21/956* (2013.01); *G01N 21/8806* (2013.01); *G01N 21/8901* (2013.01);
(Continued)

(58) Field of Classification Search
CPC ............... H05K 1/0269; H05K 13/08; H05K 2203/163; Y10T 29/49009; Y10T 29/49117; Y10T 29/49124; Y10T 29/49131; Y10T 29/49133; Y10T 29/49155; Y10T 29/49769; Y10T 29/53022; Y10T 29/53087; G06T 7/0002;
(Continued)

(56) References Cited

U.S. PATENT DOCUMENTS

2009/0114426 A1* 5/2009 Tsunekawa ...... G01N 21/95684
174/250
2010/0208250 A1* 8/2010 Ihara ...................... G01N 21/94
356/237.4
(Continued)

FOREIGN PATENT DOCUMENTS

JP    2010129696 A    6/2010
JP    2012059756 A    3/2012

*Primary Examiner* — Peter DungBa Vo
*Assistant Examiner* — Joshua D Anderson
(74) *Attorney, Agent, or Firm* — Panitch Schwarze Belisario & Nadel LLP

(57) ABSTRACT

A base insulating layer and a cover insulating layer of a first printed circuit board are formed of a first insulating material, and a base insulating layer and a cover insulating layer of a second printed circuit board are formed of a second insulating material. During inspection of the first printed circuit board, the first printed circuit board is irradiated with first light having a peak wavelength in a first wavelength range, and an image is produced based on reflected light from the first printed circuit board. During inspection of the second printed circuit board, the second printed circuit board is irradiated with second light having a peak wavelength in a second wavelength region different from the first wavelength region, and an image is produced based on reflected light from the second printed circuit board.

6 Claims, 8 Drawing Sheets

(51) Int. Cl.
　　　*H05K 3/10*　　　(2006.01)
　　　*G01N 21/89*　　(2006.01)
　　　*H05K 1/02*　　　(2006.01)
　　　*H05K 13/08*　　(2006.01)
　　　*H05K 1/05*　　　(2006.01)

(52) U.S. Cl.
　　　CPC ..... *G01N 21/95684* (2013.01); *H05K 1/0269* (2013.01); *G01N 2021/8845* (2013.01); *G01N 2021/8887* (2013.01); *G01N 2021/8909* (2013.01); *G01N 2021/95638* (2013.01); *G01N 2021/95661* (2013.01); *H05K 1/056* (2013.01); *H05K 13/08* (2013.01); *H05K 2201/0154* (2013.01); *H05K 2203/163* (2013.01); *Y10T 29/49004* (2015.01); *Y10T 29/49124* (2015.01); *Y10T 29/53022* (2015.01); *Y10T 29/53087* (2015.01)

(58) Field of Classification Search
　　　CPC ................. G06T 7/0004; G06T 7/0008; G06T 2207/10152; G06T 2207/30141; G01N 21/25; G01N 21/255; G01N 21/256; G01N 21/29; G01N 21/33; G01N 21/35; G01N 21/3581; G01N 21/359; G01N 21/88; G01N 21/8803; G01N 21/8806; G01N 21/896; G01N 21/956; G01N 21/95607; G01N 21/95684; G01N 2021/1736; G01N 2021/1753; G01N 2021/8461; G01N 2021/8854; G01N 2021/8809; G01N 2021/8816; G01N 2021/8835; G01N 2021/8845; G01N 2021/8962; G01N 2021/8965; G01N 2021/8967; G01N 2021/95638; G01N 2021/95646; G01N 2021/95653; G01N 2021/95661

See application file for complete search history.

(56)　　　　　References Cited

U.S. PATENT DOCUMENTS

| | | | |
|---|---|---|---|
| 2010/0263206 A1* | 10/2010 | Toyoda | G01N 21/94 29/829 |
| 2012/0055697 A1 | 3/2012 | Okamoto | |
| 2013/0044208 A1* | 2/2013 | Cherbis | G06K 9/209 348/125 |
| 2013/0155191 A1* | 6/2013 | Ishigaki | G01B 11/2509 348/46 |
| 2015/0040379 A1 | 2/2015 | Okamoto | |

* cited by examiner

[FIRST PRINTED CIRCUIT BOARD]

(450nm)

(730nm)

(450nm)

(730nm)

METHOD OF MANUFACTURING PRINTED CIRCUIT BOARD AND METHOD OF INSPECTING PRINTED CIRCUIT BOARD

BACKGROUND OF THE INVENTION

Field of the Invention

The present invention relates to a method of manufacturing a printed circuit board and a method of inspecting the printed circuit board.

Description of Related Art

A printed circuit board such as a suspension board having a circuit includes a metal support layer, a base insulating layer, wiring traces and a cover insulating layer in order. If a wiring trace of such a printed circuit board is defective, connection reliability is reduced. Therefore, whether the wiring traces are defective is inspected.

During the inspection, the printed circuit board is irradiated with light from a light source unit of an inspection device, and an image of the wiring traces of the printed circuit board is produced by a camera unit (see JP 2012-59756 A, for example).

BRIEF SUMMARY OF THE INVENTION

In a method of manufacturing a printed circuit board described in JP 2012-59756 A, a surface of a base insulating layer of a printed circuit board is roughened. Further, a wavelength of incident light on conductor traces (wiring traces) is adjusted to 435 nm to 500 nm, and inclined light in which the incident light is inclined with respect to its light axis is included. Thus, the incident light is scattered on the surface of the base insulating layer. Further, the light that is transmitted through the base insulating layer and reflected from a surface of the metal support layer is scattered on the surface of the base insulating layer. On the one hand, the light reflected from surfaces of the conductor traces is not scattered. As a result, the contrast between the conductor traces and the insulating layer can be improved.

However, in the method of manufacturing the above-mentioned printed circuit board, a step of roughening the surface of the base insulating layer is required. It is desired to determine whether the wiring traces are defective without adding a step of manufacturing the printed circuit board.

An object of the present invention is to provide a method of manufacturing a printed circuit board and a method of inspecting the printed circuit board capable of determining whether a wiring trace is defective with high accuracy without addition of a step of manufacturing the printed circuit board.

(1) According to one aspect of the present invention, a method of manufacturing a printed circuit board includes the steps of fabricating the printed circuit board that includes a metal support substrate, a first insulating layer, a wiring trace and a second insulating layer in order, and performing inspection of the printed circuit board, wherein the step of fabricating the printed circuit board includes fabricating a first printed circuit board in which the first and second insulating layers are formed of a first insulating material, or fabricating a second printed circuit board in which the first and second insulating layers are formed of a second insulating material, the step of performing the inspection includes irradiating the first printed circuit board with first light having a peak wavelength in a first wavelength region during inspection of the first printed circuit board, and irradiating the second printed circuit board with second light having a peak wavelength in a second wavelength region different from the first wavelength region during inspection of the second printed circuit board, producing an image of the first printed circuit board based on reflected light from the first printed circuit board during the inspection of the first printed circuit board, and producing an image of the second printed circuit board based on reflected light from the second printed circuit board during the inspection of the second printed circuit board, and determining whether the wiring trace is defective based on the image of the first printed circuit board during the inspection of the first printed circuit board, and determining whether the wiring trace is defective based on the image of the second printed circuit board during the inspection of the second printed circuit board, a ratio of light reflected by the wiring trace and emitted from the printed circuit board to light incident on the printed circuit board is defined as wiring reflectance, and a ratio of light reflected by the metal support substrate and emitted from the printed circuit board to light incident on the printed circuit board is defined as substrate reflectance, the first printed circuit board has characteristics in which a difference between the wiring reflectance and the substrate reflectance regarding the first light is larger than a difference between the wiring reflectance and the substrate reflectance regarding the second light, and the second printed circuit board has characteristics in which a difference between the wiring reflectance and the substrate reflectance regarding the second light is larger than a difference between the wiring reflectance and the substrate reflectance regarding the first light.

In the method of manufacturing the printed circuit board, the first printed circuit board or the second printed circuit board is fabricated, and then the inspection of the fabricated first or second printed circuit board is performed. During the inspection of the first printed circuit board, the first light having the peak wavelength in the first wavelength region is emitted. During the inspection of the second printed circuit board, the second light having the peak wavelength in the second wavelength region is emitted.

The difference between the wiring reflectance and the substrate reflectance in the case where the first light is incident on the first printed circuit board is larger than the difference between the wiring reflectance and the substrate reflectance in the case where the second light is incident on the first printed circuit board. In this case, the image is produced based on the first light reflected by the first printed circuit board, so that the contrast between the wiring trace and the metal support substrate is high in the image. Thus, it is possible to determine whether the wiring trace of the first printed circuit board is defective with high accuracy.

The difference between the wiring reflectance and the substrate reflectance in the case where the second light is incident on the second printed circuit board is larger than the difference between the wiring reflectance and the substrate reflectance in the case where the first light is incident on the second printed circuit board. In this case, the image is produced based on the second light reflected by the second printed circuit board, so that the contrast between the wiring trace and the metal support substrate is high in the image. Thus, it is possible to determine whether the wiring trace of the second printed circuit board is defective with high accuracy.

As a result, it is possible to determine whether the wiring traces of the printed circuit boards having different optical characteristics are defective with high accuracy without adding a manufacturing step.

(2) The first wavelength region may be not less than 425 nm and not more than 525 nm, and the second wavelength region may be not less than 630 nm and not more than 850 nm.

In this case, the difference between the wiring reflectance and the substrate reflectance in the case where the first printed circuit board is irradiated with the first light having the peak wavelength of not less than 425 nm and not more than 525 nm is larger than the difference between the wiring reflectance and the substrate reflectance in the case where the first printed circuit board is irradiated with the second light having the peak wavelength of not less than 630 nm and not more than 850 nm. Presence and absence of a defect of the wiring trace of the first printed circuit board having such optical characteristics can be determined with high accuracy.

Further, the difference between the wiring reflectance and the substrate reflectance in the case where the second printed circuit board is irradiated with the second light having the peak wavelength of not less than 630 nm and not more than 850 nm is larger than the difference between the wiring reflectance and the substrate reflectance in the case where the second printed circuit board is irradiated with the first light having the peak wavelength of not less than 425 nm and not more than 525 nm. It is possible to determine whether the wiring trace of the second printed circuit board having such optical characteristics are defective with high accuracy.

(3) The first printed circuit board may be irradiated with the first light by a first light-emitting device that generates violet light or blue light, and the second printed circuit board may be irradiated with the second light by a second light-emitting device that generates red light or infrared light.

In this case, the first printed circuit board can be easily irradiated with the first light having the peak wavelength of not less than 425 nm and not more than 525 nm. Further, the second printed circuit board can be easily irradiated with the second light having the peak wavelength of not less than 630 nm and not more than 850 nm.

(4) The first insulating material may have a light transmittance higher than that of the second insulating layer at each wavelength in a range of not less than 425 nm and not more than 850 nm.

In this case, the light transmittances of the first and second insulating layers in the first printed circuit board are higher than the light transmittances of the first and second insulating layers in the second printed circuit board. It is possible to determine whether the wiring trace of the printed circuit boards having such different optical characteristics is defective with high accuracy.

(5) The light transmittances of the first and second insulating materials may increase as wavelengths of light increase in the range of not less than 425 nm and not more than 850 nm.

In this case, the difference between the wiring reflectance and the substrate reflectance in the case where the first light is incident on the first printed circuit board is larger than the difference between the wiring reflectance and the substrate reflectance in the case where the second light is incident on the first printed circuit board. Further, the difference between the wiring reflectance and the substrate reflectance in the case where the second light is incident on the second printed circuit board is larger than the difference between the wiring reflectance and the substrate reflectance in the case where the first light is incident on the second printed circuit board. It is possible to determine whether the wiring traces of the printed circuit boards having such different optical characteristics are defective with high accuracy.

(6) According to another aspect of the present invention, a method of inspecting a printed circuit board that includes a metal support substrate, a first insulating layer, a wiring trace and a second insulating layer in order, wherein the printed circuit board is a first printed circuit board in which the first and second insulating layers are formed of a first insulating material or a second printed circuit board in which the first and second insulating layers are formed of a second insulating material, the method of inspecting the printed circuit board includes the steps of irradiating the first printed circuit board with first light having a peak wavelength in a first wavelength region during inspection of the first printed circuit board, and irradiating the second printed circuit board with second light having a peak wavelength in a second wavelength region different from the first wavelength region during inspection of the second printed circuit board, producing an image of the first printed circuit board based on reflected light from the first printed circuit board during the inspection of the first printed circuit board, and producing an image of the second printed circuit board based on reflected light from the second printed circuit board during the inspection of the second printed circuit board, and determining whether the wiring trace is defective based on the image of the first printed circuit board during the inspection of the first printed circuit board, and determining whether the wiring trace is defective based on the image of the second printed circuit board during the inspection of the second printed circuit board, a ratio of light reflected by the wiring trace and emitted from the printed circuit board to light incident on the printed circuit board is defined as wiring reflectance, and a ratio of light reflected by the metal support substrate and emitted from the printed circuit board to light incident on the printed circuit board is defined as substrate reflectance, the first printed circuit board has characteristics in which a difference between the wiring reflectance and the substrate reflectance regarding the first light is larger than a difference between the wiring reflectance and the substrate reflectance regarding the second light, and the second printed circuit board has characteristics in which a difference between the wiring reflectance and the substrate reflectance regarding the second light is larger than a difference between the wiring reflectance and the substrate reflectance regarding the first light.

In the method of inspecting the printed circuit board, the first light having the peak wavelength in the first wavelength region is emitted during the inspection of the first printed circuit board. In the method of inspecting the printed circuit board, the second light having the peak wavelength in the second wavelength region is emitted during the inspection of the second printed circuit board.

The difference between the wiring reflectance and the substrate reflectance in the case where the first light is incident on the first printed circuit board is larger than the difference between the wiring reflectance and the substrate reflectance in the case where the second light is incident on the first printed circuit board. In this case, the image is produced based on the first light reflected by the first printed circuit board, so that the contrast between the wiring trace and the metal support substrate is high in the image. Thus, it is possible to determine whether the wiring trace of the first printed circuit board are defective with high accuracy.

The difference between the wiring reflectance and the substrate reflectance in the case where the second light is incident on the second printed circuit board is larger than the difference between the wiring reflectance and the substrate reflectance in the case where the first light is incident on the second printed circuit board. In this case, the image is produced based on the second light reflected by the second printed circuit board, so that the contrast between the wiring trace and the metal support substrate is high in the image. Thus, it is possible to determine whether the wiring trace of the second printed circuit board are defective with high accuracy.

As a result, it is possible to determine whether the wiring traces of the printed circuit boards having different optical characteristics are defective with high accuracy without adding a manufacturing step.

Other features, elements, characteristics, and advantages of the present invention will become more apparent from the following description of preferred embodiments of the present invention with reference to the attached drawings.

DESCRIPTION OF THE PREFERRED EMBODIMENTS

A method of manufacturing a printed circuit board and a method of inspecting the printed circuit board according to embodiments of the present invention will be described below with reference to drawings. The method of manufacturing the printed circuit board includes steps of manufacturing the printed circuit board and steps of inspecting the printed circuit board. The printed circuit board is a suspension board having a circuit, for example.

(1) Manufacturing Process of Printed Circuit Board

Figure 1A:
FIGS. 1A to 1D are cross sectional views showing one example of a manufacturing process of a printed circuit board according to the present embodiment.

FIGS. 1A to 1D are cross sectional views showing one example of the manufacturing process of the printed circuit board according to the present embodiment. First, as shown in FIG. 1A, an elongated metal support substrate 11 made of stainless is prepared. While the manufacturing process of the one printed circuit board is shown in FIGS. 1A to 1D, the plurality of printed circuit boards are formed on the elongated metal support substrate 11 by a roll-to-roll system in the present embodiment. The thickness of the metal support substrate 11 is not less than 5 μm and not more than 50 μm, for example, and is preferably not less than 10 μm and not more than 30 μm.

Figure 1B:

Next, as shown in FIG. 1B, a base insulating layer 12 made of first polyimide or second polyimide is formed on the metal support substrate 11. The first and second polyimide will be described below. The base insulating layer 12 is one example of a first insulating layer. The thickness of the base insulating layer 12 is not less than 1 μm and not more than 30 μm, for example, and is preferably not less than 3 μm and not more than 20 μm.

Figure 1C:
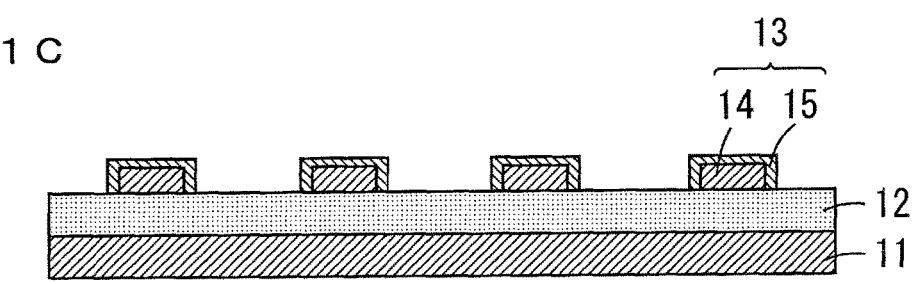

Then, as shown in FIG. 1C, a plurality of wiring traces 13 are formed on the base insulating layer 12. In the present embodiment, each of wiring traces 13 is constituted by conductor traces 14 made of copper and metal cover layers 15 made of nickel. The thickness of the wiring traces 13 is not less than 3 μm and not more than 30 μm, for example, and preferably not less than 5 μm and not more than 20 μm. Each wiring trace 13 includes a line wiring layer and terminal portions such as pads provided at both ends of the wiring layer. The wiring trace 13 may be a grounding conductor layer. Each conductor trace 14 may be formed using a semi-additive method, for example, or may be formed using another method such as a subtractive method. The metal cover layer 15 is formed to cover a surface of the conductor trace 14 by electroless plating, for example. The thickness of the metal cover layers 15 is not more than 2 μm, for example, and is preferably not less than 0.1 μm and not more than 1 μm.

Figure 1D:
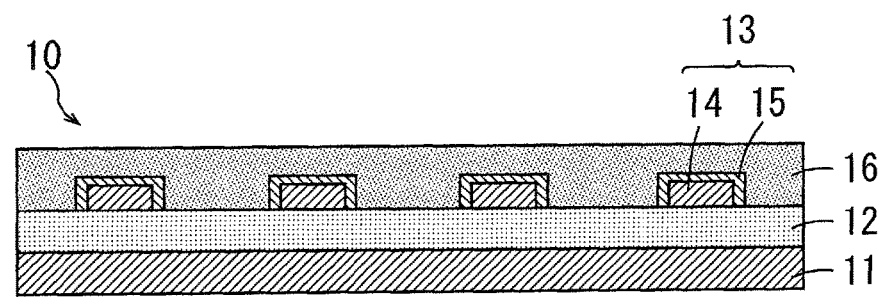

As shown in FIG. 1D, a cover insulating layer 16 made of the first polyimide or the second polyimide is formed on the base insulating layer 12 to cover the plurality of wiring traces 13. In this case, openings are provided at the cover insulating layer 16 such that each terminal portion of the wiring trace 13 is exposed. The cover insulating layer 16 is one example of a second insulating layer. The thickness of the cover insulating layer 16 is not less than 3 μm and not more than 30 μm, for example, and is preferably not less than 5 μm and not more than 20 μm.

(2) Characteristics of First and Second Polyimide

Figure 2:
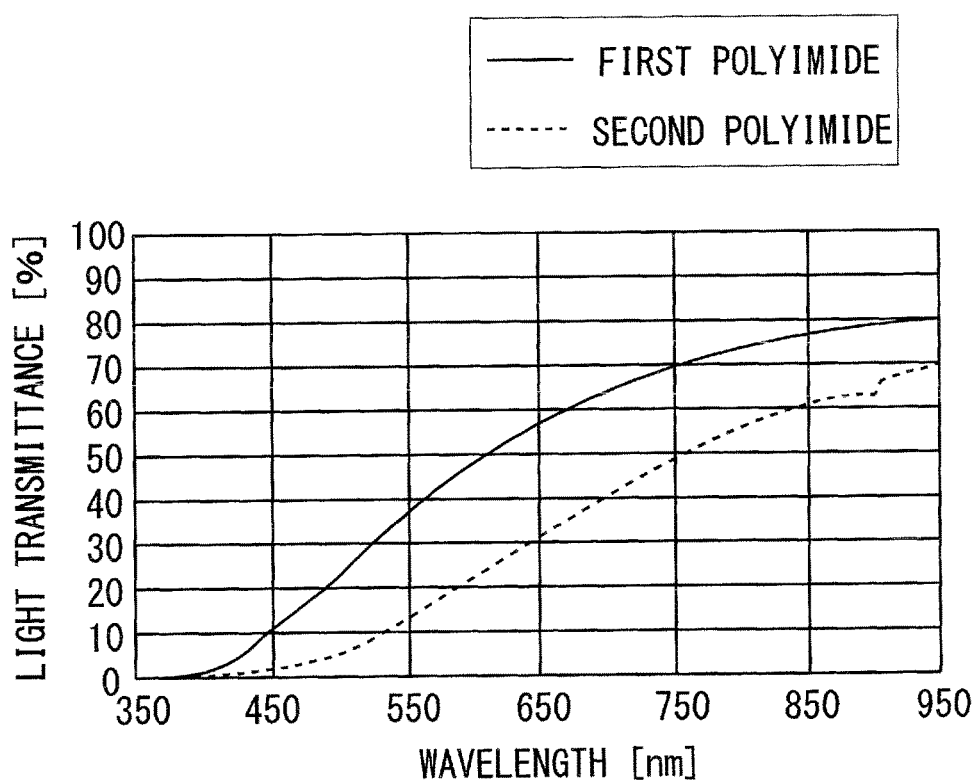
FIG. 2 is a diagram showing spectral characteristics of first and second polyimide.

FIG. 2 is a diagram showing spectral characteristics of the first and second polyimide. The ordinate of FIG. 2 indicates a light transmittance, and the abscissa indicates a wavelength of light. In FIG. 2, a solid line indicates a light transmittance of the first polyimide, and a dotted line indicates a light transmittance of the second polyimide. The thickness of each of the first and second polyimide is 15 μm. Further, a relationship between the wavelength of light and the light transmittance regarding each of the first and second polyimide is shown in the Table 1.

TABLE 1

| Wavelength | Light Transmittance [%] | |
|---|---|---|
| (nm) | First Polyimide | Second Polyimide |
| 400 | 0.15 | 0.01 |
| 425 | 3.52 | 0.19 |
| 430 | 4.73 | 0.32 |
| 450 | 9.77 | 1.23 |
| 500 | 22.84 | 5.43 |
| 525 | 29.69 | 8.65 |

TABLE 1-continued

| Wavelength | Light Transmittance [%] | |
|---|---|---|
| (nm) | First Polyimide | Second Polyimide |
| 550 | 36.32 | 12.58 |
| 600 | 47.91 | 21.64 |
| 630 | 53.55 | 27.31 |
| 650 | 56.85 | 31.05 |
| 700 | 63.80 | 40.01 |
| 750 | 69.23 | 48.30 |
| 800 | 73.37 | 55.29 |
| 850 | 76.40 | 60.97 |
| 900 | 77.80 | 63.28 |

As shown in FIG. 2 and the Table 1, the light transmittance of the first polyimide is higher than that of the second polyimide at each wavelength in a range from the wavelength of 400 nm to the wavelength of 950 nm. Further, the light transmittance of the first polyimide monotonously increases as the wavelength increases. Similarly, the light transmittance of the second polyimide monotonously increases as the wavelength increases.

At the wavelength of 425 nm, the light transmittance of the first polyimide is 3.52%, and the light transmittance of the second polyimide is 0.19%. At the wavelength of 450 nm, the light transmittance of the first polyimide is 9.77%, and the light transmittance of the second polyimide is 1.23%. At the wavelength of 500 nm, the light transmittance of the first polyimide is 22.84%, and the light transmittance of the second polyimide is 5.43%. At the wavelength of 525 nm, the light transmittance of the first polyimide is 29.69%, and the light transmittance of the second polyimide is 8.65%. At the wavelength of 630 nm, the light transmittance of the first polyimide is 53.55%, and the light transmittance of the second polyimide is 27.31%. At the wavelength of 700 nm, the light transmittance of the first polyimide is 63.80%, and the light transmittance of the second polyimide is 40.01%. At the wavelength of 850 nm, the light transmittance of the first polyimide is 76.40%, and the light transmittance of the second polyimide is 60.97%.

The printed circuit board 10 in which the base insulating layer 12 and the cover insulating layer 16 are formed of the first polyimide is referred to as a first printed circuit board 10a, and the printed circuit board 10 in which the base insulating layer 12 and the cover insulating layer 16 are formed of the second polyimide is referred to as a second printed circuit board 10b.

(3) Inspection Device for Printed Circuit Board and Inspecting Process of Printed Circuit Board An elongated board assembly sheet having the plurality of printed circuit boards 10 is fabricated by the steps of the above-mentioned FIGS. 1A to 1D. Next, inspection of the wiring traces 13 of each printed circuit board 10 of the board assembly sheet is performed.

Figure 3A:
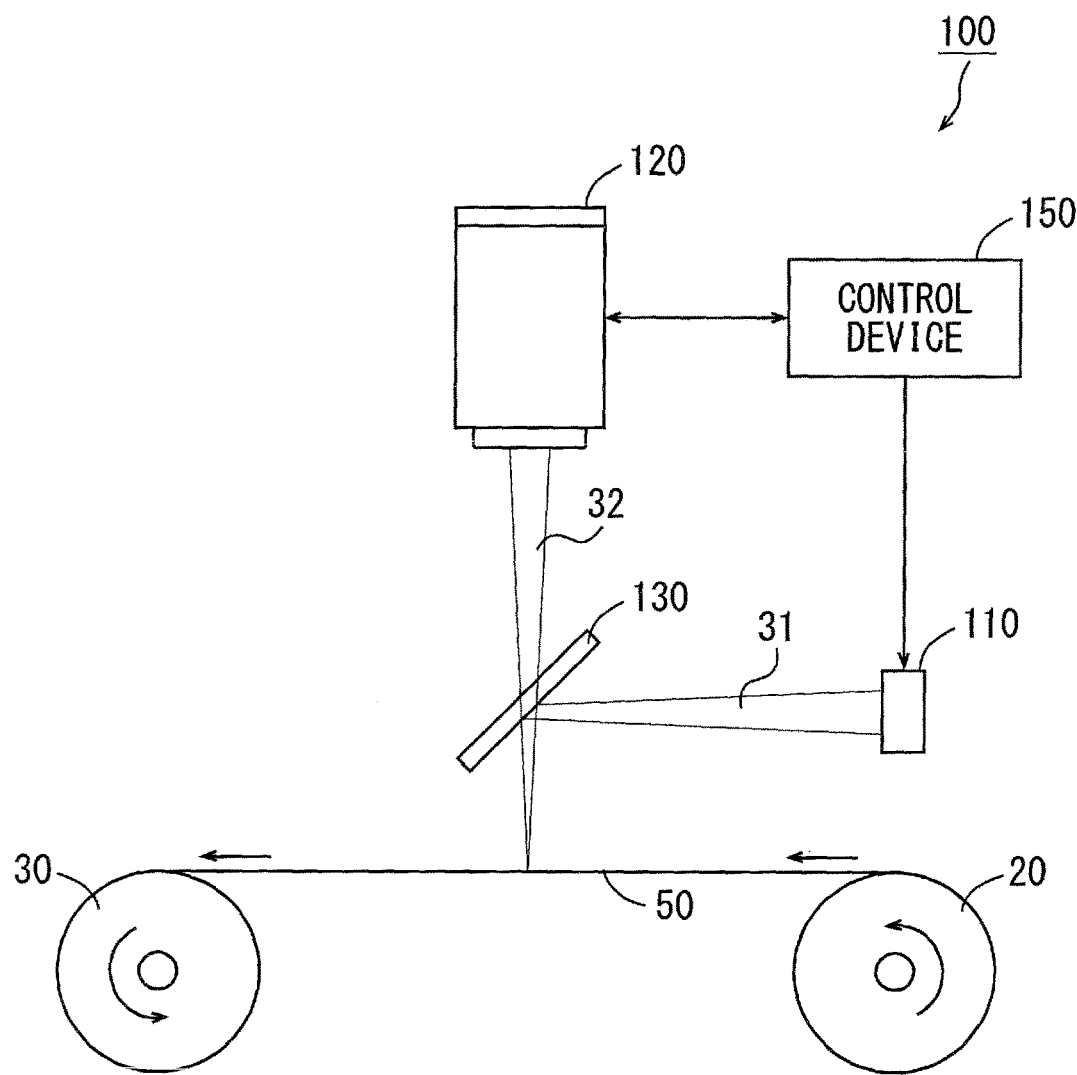
FIG. 3A is a side view of an inspection device for inspecting a board assembly sheet transported by a roll-to-roll system.
Figure 3B:
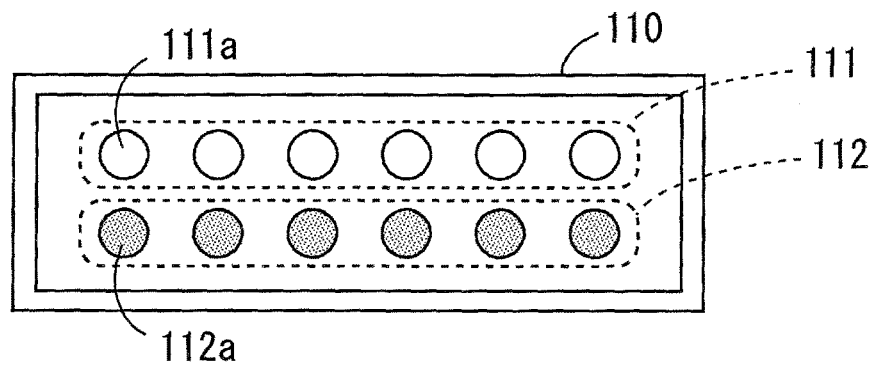
FIG. 3B is a front view of a light source device of the inspection device of FIG. 3A.

FIGS. 3A and 3B are schematic diagrams showing the inspection device for the printed circuit board, FIG. 3A shows a side view of the inspection device for inspecting the board assembly sheet transported by the roll-to-roll system, and FIG. 3B shows a front view of a light source device of the inspection device of FIG. 3A.

As shown in FIG. 3A, a feed roll 20 and a wind-up roll 30 are arranged at a distance to be rotatable in a direction of arrows. The board assembly sheet 50 fed from the feed roll 20 is transported in a direction of arrows and is wound by the wind-up roll 30. The inspection device 100 includes the light source device 110, an imaging device 120, a half mirror 130 and a control device 150.

The half mirror 130 is arranged to form an angle of substantially 45 degrees with respect to a surface of the board assembly sheet 50 directly upward of the transported board assembly sheet 50. The light source device 110 is arranged to be opposite to the half mirror 130. The imaging device 120 is arranged directly upward of the half mirror 130.

The light source device 110 emits incident light 31 in parallel with the surface of the board assembly sheet 50 towards the half mirror 130. The half mirror 130 reflects the incident light 31 downward. Thus, the incident light 31 is incident on the surface of the board assembly sheet 50. The half mirror 130 transmits reflected light 32 from the board assembly sheet 50, and the reflected light 32 is incident on the imaging device 120. Thus, an image of each printed circuit board 10 of the board assembly sheet 50 is acquired by the imaging device 120.

As shown in FIG. 3B, the light source device 110 includes a first light source 111 that emits first light and a second light source 112 that emits second light. The first light has a peak wavelength in a first wavelength region. In the present embodiment, the first wavelength region is from 425 nm to 525 nm. The second light has a peak wavelength in a second wavelength region. In the present embodiment, the second wavelength region is from 630 nm to 850 nm. In the present embodiment, a plurality of light-emitting diodes 111a that emit violet light or blue light, for example, are used as the first light source 111. As the second light source 112, a plurality of light-emitting diodes 112a that emit red light or infrared light are used, for example. The plurality of light-emitting diodes 111a are arranged in a horizontal direction. The plurality of light-emitting diodes 112a are arranged in parallel with the plurality of light-emitting diodes 111a in the horizontal direction. The first light source 111 and the second light source 112 are selectively turned on and off.

When the first light source 111 is turned on, the printed circuit boards 10 of the board assembly sheet 50 are irradiated with the first light being emitted as the incident light 31. When the first light source 111 is turned on, the second light source 112 is turned off. When the second light source 112 is turned on, the printed circuit boards 10 of the board assembly sheet 50 are irradiated with the second light being emitted as the incident light 31. When the second light source 112 is turned on, the first light source 111 is turned off. Thus, the wavelength regions of the incident light 31 with which the printed circuit boards 10 are irradiated with are switched.

The control device 150 is constituted by a CPU (Central Processing Unit) and a semiconductor memory, for example. This control device 150 controls operations of the feed roll 20, the wind-up roll 30, the light source device 110 and the imaging device 120, and performs automatic optical inspection based on images, described below.

In a case in which the board assembly sheet 50 includes the plurality of first printed circuit boards 10a as the plurality of printed circuit boards 10, the first light source 111 is turned on. In a case in which the board assembly sheet 50 includes the plurality of second printed circuit boards 10b as the plurality of printed circuit boards 10, the second light source 112 is turned on. Switching between the first light source 111 and the second light source 112 may be performed by an operator, or may be automatically performed by the control device 150 in accordance with a computer program.

Figure 4A:
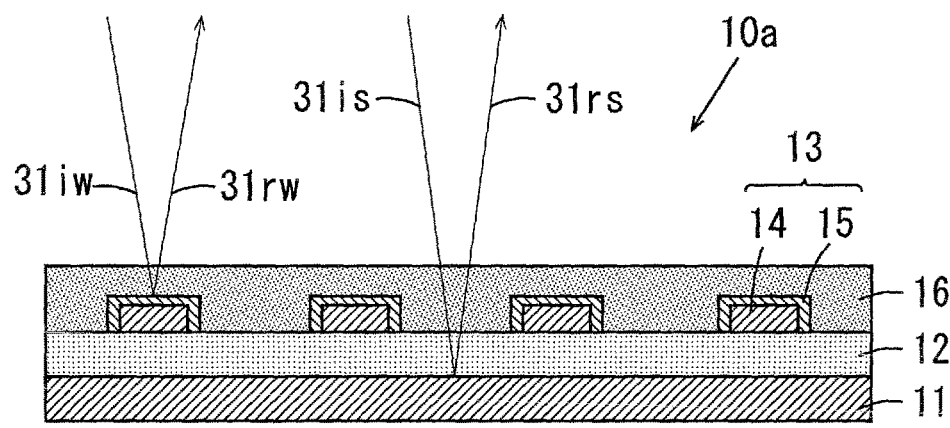
FIG. 4A is a diagram showing a step of inspecting a first printed circuit board.
Figure 4B:
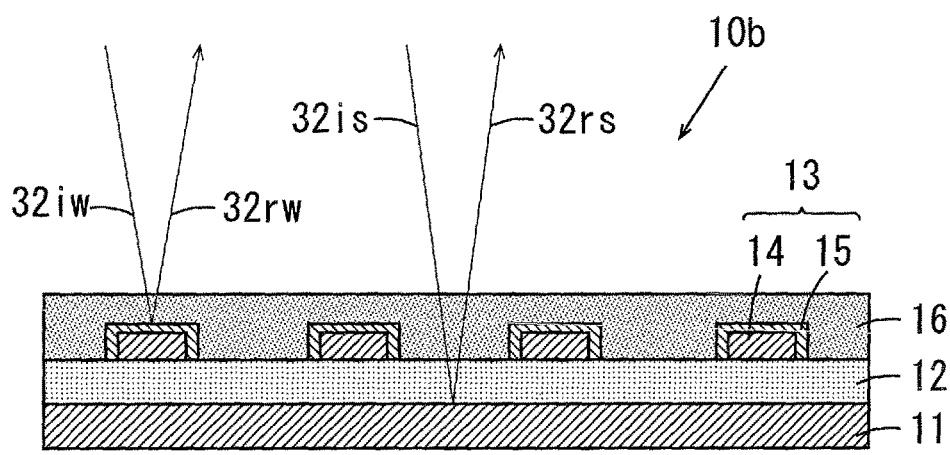
FIG. 4B is a diagram showing a step of inspecting a second printed circuit board.

FIG. 4A is a diagram showing a step of inspecting the first printed circuit board 10a, and FIG. 4B is a diagram showing a step of inspecting the second printed circuit board 10b.

During the inspection of the first printed circuit board 10a, the first printed circuit board 10a is irradiated with the first light by the inspection device 100 of FIGS. 3A and 3B. In FIG. 4A, the first light incident on the wiring traces 13 is referred to as wiring incident light 31iw, and the first light reflected from the wiring traces 13 is referred to as wiring reflected light 31rw. Further, the first light incident on the metal support substrate 11 is referred to as substrate incident light 31is, and the first light reflected from the metal support substrate 11 is referred to as substrate reflected light 31rs.

The cover insulating layer 16 transmits the wiring incident light 31iw, and the wiring incident light 31iw is incident on the wiring traces 13. The cover insulating layer 16 transmits the wiring reflected light 31rw, and the wiring reflected light 31rw is incident on the imaging device 120. The cover insulating layer 16 and the base insulating layer 12 transmit the substrate incident light 31Is, and the substrate incident light 31is is incident on the metal support substrate 11. The base insulating layer 12 and the cover insulating layer 16 transmit the substrate reflected light 31rs, and the substrate reflected light 31rs is incident on the imaging device 120. The imaging device 120 produces an image of the first printed circuit board 10a based on the wiring reflected light 31rw and the substrate reflected light 31rs.

An intensity ratio of the wiring reflected light 31rw to the wiring incident light 31iw is referred to as wiring reflectance R1w. Further, an intensity ratio of the substrate reflected light 31rs to the substrate incident light 31is is referred to as substrate reflectance R1s.

During inspection of the second printed circuit board 10b, the second printed circuit board 10b is irradiated with the second light by the inspection device 100 of FIGS. 3A and 3B. In FIG. 4B, the second light incident on the wiring traces 13 is referred to as wiring incident light 32iw, and the second light reflected from the wiring traces 13 is referred to as wiring reflected light 32rw. Further, the second light incident on the metal support substrate 11 is referred to as substrate incident light 32is, and the second light reflected from the metal support substrate 11 is referred to as substrate reflected light 32rs.

The cover insulating layer 16 transmits the wiring incident light 32iw, and the wiring incident light 32iw is incident on the wiring traces 13. The cover insulating layer 16 transmits the wiring reflected light 32rw, and the wiring reflected light 32rw is incident on the imaging device 120. The cover insulating layer 16 and the base insulating layer 12 transmit the substrate incident light 32is, and the substrate incident light 32is is incident on the metal support substrate 11. The base insulating layer 12 and the cover insulating layer 16 transmit the substrate reflected light 32rs, and the substrate reflected light 32rs is incident on the imaging device 120. The imaging device 120 produces an image of the second printed circuit board 10b based on the wiring reflected light 32rw and the substrate reflected light 32rs.

An intensity ratio of the wiring reflected light 32rw to the wiring incident light 32iw is referred to as wiring reflectance R2w. Further, an intensity ratio of the substrate reflected light 32rs to the substrate incident light 32is is referred to as substrate reflectance R2s.

(4) Optical Characteristics of First and Second Printed Circuit Boards

Figure 5:
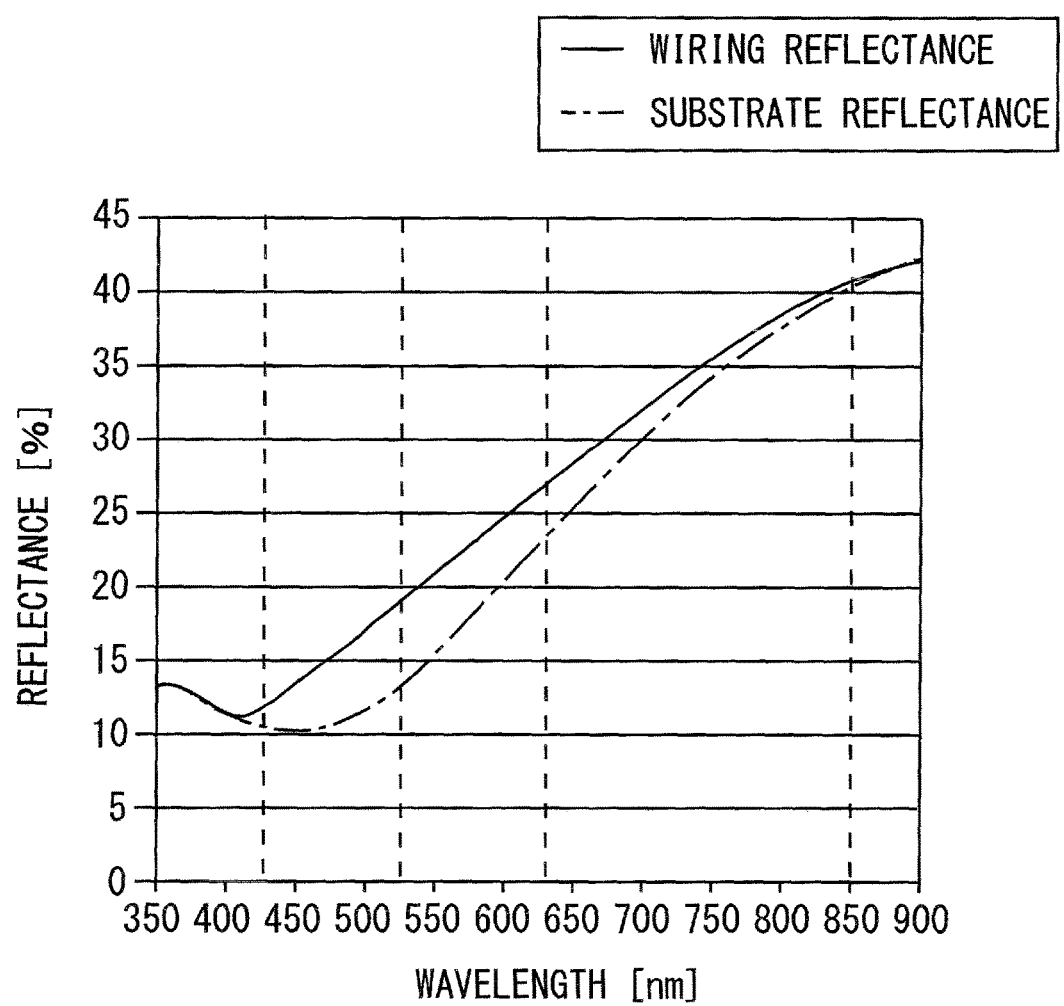
FIG. 5 is a diagram showing a relationship between reflectance of light and a wavelength of light regarding the first printed circuit board.
Figure 6:
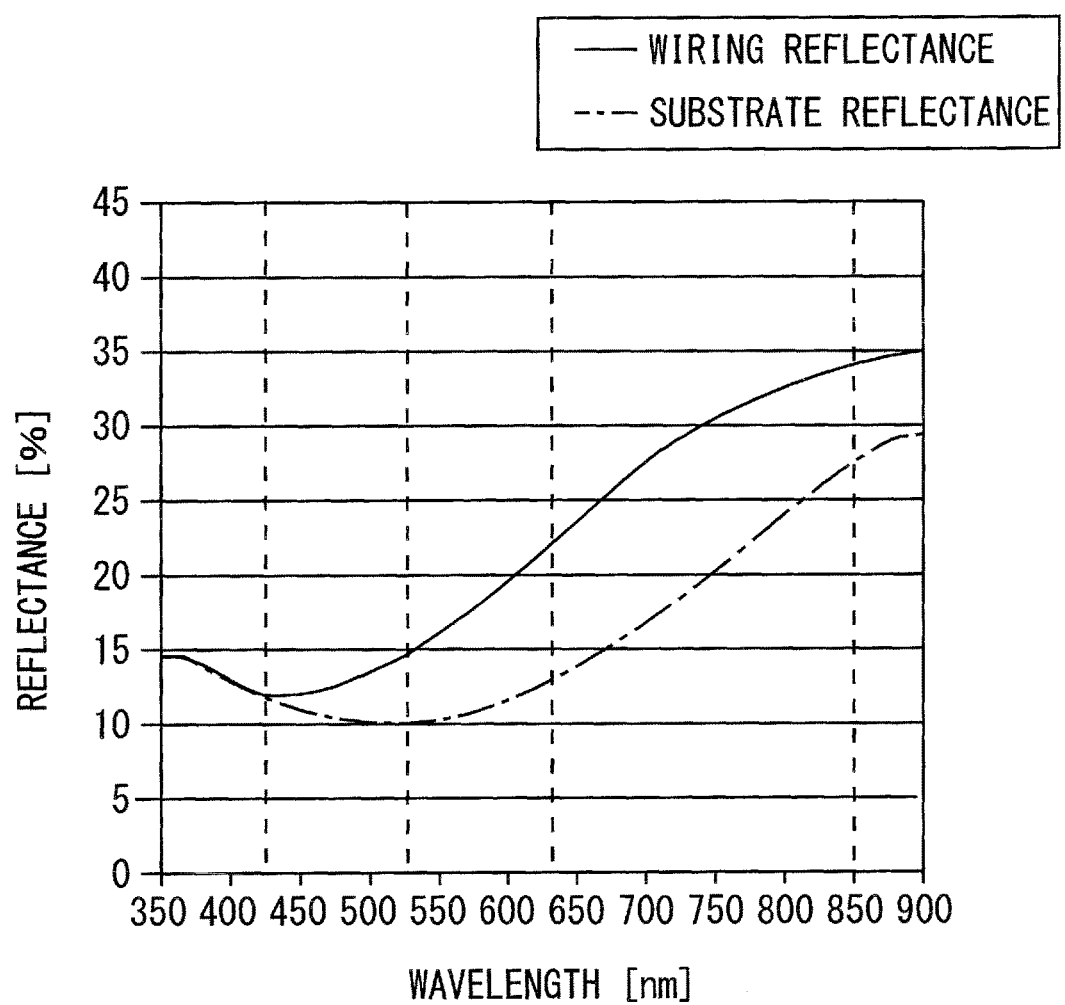
FIG. 6 is a diagram showing a relationship between reflectance of light and a wavelength of light regarding the second printed circuit board.

FIG. 5 is a diagram showing a relationship between reflectance of light and a wavelength of light regarding the first printed circuit board 10a. In FIG. 5, the wiring reflectance is indicated by a solid line, and the substrate reflectance is indicated by a one-dot and dash line. Further, FIG. 6 is a diagram showing a relationship between reflectance of light and a wavelength of light regarding the second printed circuit board 10b. In FIG. 6, the wiring reflectance is indicated by a solid line, and the substrate reflectance is indicated by a one-dot and dash line.

As shown in FIG. 5, regarding the first printed circuit board 10a, a difference between the wiring reflectance and the substrate reflectance is ensured to be not less than about 2% in the first wavelength region from 425 nm to 525 nm. In contrast, a difference between the wiring reflectance and the substrate reflectance is not ensured in the second wavelength region from 630 nm to 850 nm.

In this manner, the first printed circuit board 10a has characteristics in which the difference between the wiring reflectance R1w and the substrate reflectance R1s for the first light is larger than the difference between the wiring reflectance R2w and the substrate reflectance R2s for the second light.

Therefore, when the first printed circuit board 10a is inspected, the first light having a peak wavelength in the first wavelength region of not less than 425 nm and not more than 525 nm is used. Thus, the contrast between the wiring traces 13 and the metal support substrate 11 is high in the image acquired by the imaging device 120. In particular, the first light having the peak wavelength in the wavelength region of not less than 450 nm and not more than 525 nm is preferably used. Thus, the contrast between the wiring traces 13 and the metal support substrate 11 is higher in the image acquired by the imaging device 120.

As shown in FIG. 6, regarding the second printed circuit board 10b, a difference between the wiring reflectance and the substrate reflectance is ensured to be not less than about 7% in the second wavelength region from 630 nm to 850 nm. In contrast, a difference between the wiring reflectance and the substrate reflectance is small in the first wavelength region from 425 nm to 525 nm as compared to the second wavelength region from 630 nm to 850 nm.

In this manner, the second printed circuit board 10b has characteristics in which the difference between the wiring reflectance R2w and the substrate reflectance R2s for the second light is larger than the difference between the wiring reflectance R1w and the substrate reflectance R1s for the first light.

Therefore, when the second printed circuit board 10b is inspected, the second light having the peak wavelength in the second wavelength region of not less than 630 nm and not more than 850 nm is used. Thus, the contrast between the wiring traces 13 and the metal support substrate 11 is high in the image acquired by the imaging device 120. In particular, the second light having the peak wavelength in the wavelength region of not less than 630 nm and not more than 680 nm is preferably used. Thus, the contrast between the wiring traces 13 and the metal support substrate 11 is higher in the image acquired by the imaging device 120.

Figure 7A:
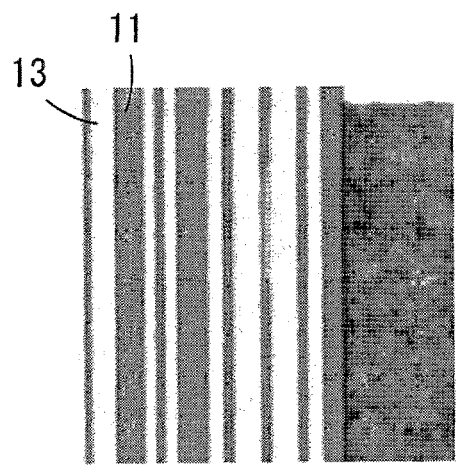
FIGS. 7A and 7B are diagrams showing examples of images acquired by an imaging device when the first printed circuit board is irradiated with first light and second light.
Figure 7B:
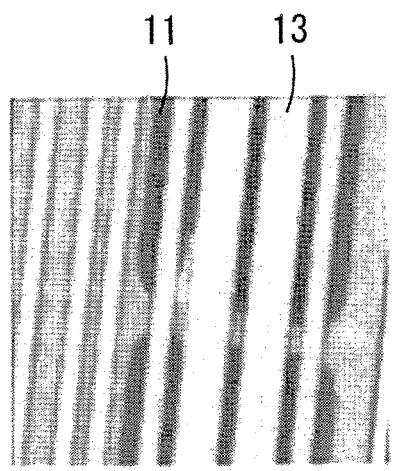
Figure 8A:
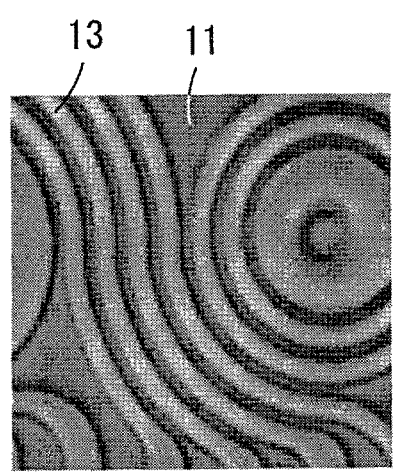
FIGS. 8A and 8B are diagrams showing examples of images acquired by the imaging device when the second printed circuit board is irradiated with the first light and the second light.
Figure 8B:
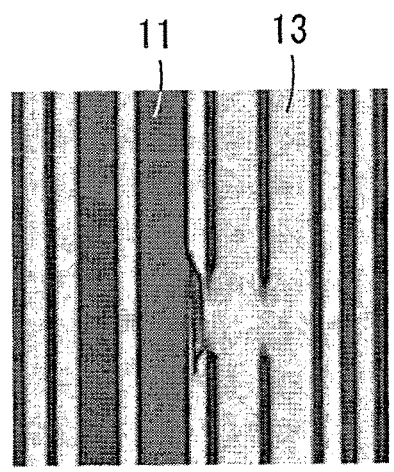

FIGS. 7A and 7B are diagrams showing examples of the images acquired by the imaging device 120 when the first printed circuit board 10a is irradiated with each of the first light and the second light. FIGS. 8A and 8B are diagrams showing examples of the images acquired by the imaging device 120 when the second printed circuit board 10b is irradiated with each of the first light and the second light.

The example of FIG. 7A is an image acquired when the first printed circuit board 10a is irradiated with the first light having a peak wavelength of 450 nm. The example of FIG. 7B is an image acquired when the first printed circuit board 10a is irradiated with the second light having a peak wavelength of 730 nm. The example of FIG. 8A is an image acquired when the second printed circuit board 10b is irradiated with the first light having the peak wavelength of 450 nm. The example of FIG. 8B is an image acquired when the second printed circuit board 10b is irradiated with the second light having a peak wavelength of 730 nm.

In the example of the first printed circuit board 10a of FIG. 7A, the difference between the wiring reflectance and the substrate reflectance for the first light is large, so that the contrast between the wiring traces 13 and the metal support substrate 11 is high in the image. Thus, the wiring traces 13 are clearly shown. In the example of the first printed circuit board 10a of FIG. 7B, the difference between the wiring reflectance and the substrate reflectance for the second light is small, so that the contrast between the wiring traces 13 and the metal support substrate 11 is low in the image. Thus, the wiring traces 13 are unclear.

In contrast, in the example of the second printed circuit board 10b of FIG. 8A, the difference between the wiring reflectance and the substrate reflectance for the first light is small, so that the contrast between the wiring traces 13 and the metal support substrate 11 is low in the image. Thus, the wiring traces 13 are unclear. In the example of the second printed circuit board 10b of FIG. 8B, the difference between the wiring reflectance and the substrate reflectance for the second light is large, so that the contrast between the wiring traces 13 and the metal support substrate 11 is high in the image. Thus, the wiring traces 13 are clearly shown.

(5) Effects of Embodiments

As described above, in a case in which the board assembly sheet 50 includes the plurality of first printed circuit boards 10a, the first light source 111 of the light source device 110 is turned on, and the image of each first printed circuit board 10a is produced by the imaging device 120. In this case, the contrast between the wiring traces 13 and the metal support substrate 11 is improved in the image. Therefore, it is possible to determine whether the wiring traces 13 of the first printed circuit board 10a are defective with high accuracy without adding a manufacturing step. For example, presence and absence of a defect such as a short-circuit between the wiring traces 13, disconnection, thinning or contamination of the wiring traces 13 in the first printed circuit board 10a can be determined with high accuracy based on the produced image.

Further, in a case in which the board assembly sheet 50 includes the plurality of second printed circuit boards 10b, the second light source 112 of the light source device 110 is turned on, and the image of each second printed circuit board 10b is produced by the imaging device 120. In this case, the contrast between the wiring traces 13 and the metal support substrate 11 in the image is improved. Therefore, it is possible to determine whether the wiring traces 13 of the second printed circuit board 10b are defective with high accuracy without adding a manufacturing step. For example, presence or absence of a defect such as a short-circuit between the wiring traces 13, disconnection, thinning or contamination of the wiring traces 13 of the second printed circuit board 10b can be determined with high accuracy based on the produced image.

(6) Inventive Example

The first printed circuit board 10a and the second printed circuit board 10b were fabricated by the manufacturing process of FIGS. 1A to 1D in the above-mentioned embodiment, and inspection was performed by the inspection device 100 of FIGS. 3A and 3B. In the inspection, images of the first printed circuit board 10a and the second printed circuit board 10b were produced by the imaging device 120 selectively using various types of light-emitting devices as the light sources of the light source device 110. As the incident light, blue light having a peak wavelength of 450 nm, red light and near-infrared light having peak wavelengths in a wavelength region from 680 nm to 850 nm, near-infrared light and far-infrared light having peak wavelengths longer than 850 nm, and white light having a wavelength component ranging from 380 nm to 780 nm were used. An angle of incidence of the incident light on each of the first printed circuit board 10a and the second printed circuit board 10b is in a range from 0 to 15°.

Results of determination regarding whether images are good are shown in the Table 2.

TABLE 2

| Light Source | Wavelength (nm) | First Printed Circuit Board <First Polyimide> | Second Printed Circuit Board <Second Polyimide> |
|---|---|---|---|
| Blue Light | 450 | ○ | x |
| Red Light and Near-Infrared Light | 680 to 850 | x | ○ |
| Near-Infrared Light and Far-Infrared Light | >850 | x | x |
| White Light | 380 to 780 | x | x |

In the Table 2, "○" indicates that the wiring traces 13 are clear in the image, and "x" indicates that the wiring traces 13 are not clear in the image.

As shown in the Table 2, when the blue incident light having the peak wavelength of 450 nm was used for the inspection of the first printed circuit board 10a, boundaries between the wiring traces 13 and the metal support substrate 11 were clear in the image. When the red incident light and the near-infrared incident light having the peak wavelengths in the wavelength range from 680 nm to 850 nm were used for the inspection of the first printed circuit board 10a, the boundaries between the wiring traces 13 and the metal support substrate 11 were unclear in the image due to the reflected light from the metal support substrate 11. When the near-infrared incident light and the far-infrared incident light having the peak wavelengths of larger than 850 nm were used for the inspection of the first printed circuit board 10a, the boundaries between the wiring traces 13 and the metal support substrate 11 were unclear in the image due to the reflected light from the metal support substrate 11. When the white incident light including the wavelength component ranging from 380 nm to 780 nm was used for the inspection of the first printed circuit board 10a, lack of brightness uniformity of the wiring traces 13 occurred, and the boundaries between the wiring traces 13 and the metal support substrate 11 were unclear in the image due to the reflected light from the metal support substrate 11.

When the blue incident light having the peak wavelength of 450 nm was used for the inspection of the second printed circuit board 10b, the boundaries between the wiring traces 13 and the metal support substrate 11 were unclear in the image due to insufficient brightness. When the red incident light and the near-infrared incident light having the peak wavelengths in the wavelength range from 680 nm to 850 nm were used for the inspection of the second printed circuit board 10b, the boundaries between the wiring traces 13 and the metal support substrate 11 were clear in the image. When the near-infrared incident light and the far-flared incident light having the peak wavelengths larger than 850 nm were used for the inspection of the second printed circuit board 10b, the boundaries between the wiring traces 13 and the metal support substrate 11 were unclear in the image due to the reflected light from the metal support substrate 11. When the white incident light including the wavelength component ranging from 380 nm to 780 nm was used for the inspection of the second printed circuit board 10b, lack of brightness uniformity of the wiring traces 13 occurred in the image.

From the above-mentioned results, during the inspection of the first printed circuit board 10a, it is possible to determine whether the wiring traces 13 are defective with high accuracy by using the violet or blue incident light having the peak wavelength (450 nm in the present example) in the first wavelength region from 425 nm to 525 nm. On the one hand, during the inspection of the second printed circuit board 10b, it is possible to determine whether the wiring traces 13 are defective with high accuracy by using the red or near-infrared incident light having the peak wavelength in the second wavelength region from 630 nm to 850 nm (from 650 nm to 850 nm in the present example).

(7) Other Embodiments

Figure 9A:
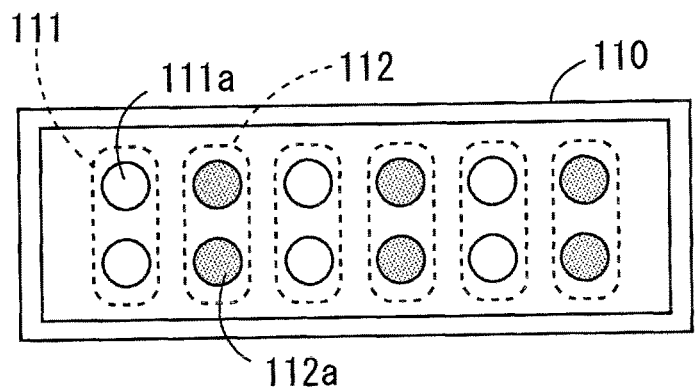
FIGS. 9A to 9C are schematic diagrams showing other examples of an arrangement of a first light source and a second light source in the light source device.
Figure 9B:
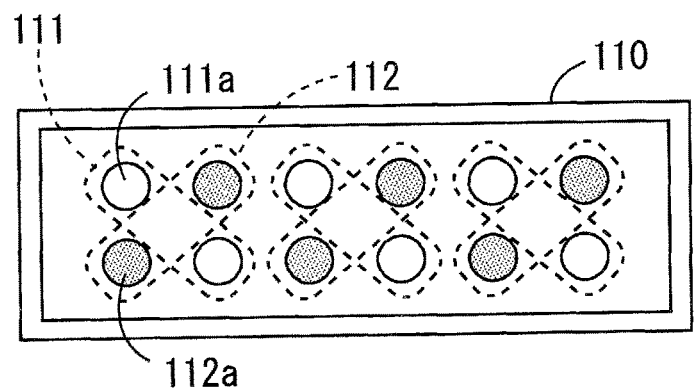
Figure 9C:
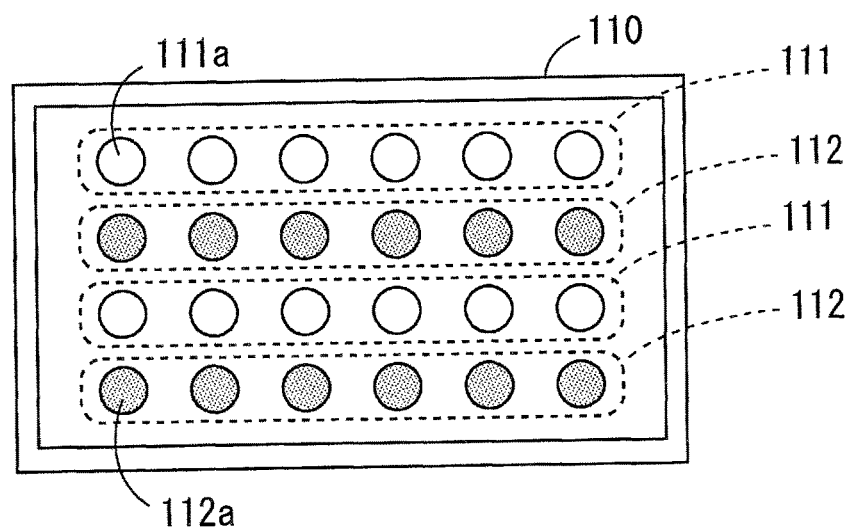

An arrangement of the first light source 111 and the second light source 112 in the light source device 110 is not limited to the arrangement of FIG. 3B in the above-mentioned embodiment. FIGS. 9A, 9B and 9C are schematic diagrams showing other examples of the arrangement of the first light source 111 and the second light source 112 in the light source device 110.

In the examples of FIGS. 9A and 9B, the plurality of light-emitting diodes 111a and the plurality of light-emitting diodes 112a are alternately arranged in the horizontal direction in a first row, and the plurality of light-emitting diodes 111a and the plurality of light-emitting diodes 112a are alternately arranged in the horizontal direction in a second row. In the example of FIG. 9A, each light-emitting diode 111a of the first row and each light-emitting diode 111a of the second row are arranged in a top-and-bottom direction, and each light-emitting diode 112a of the first row and each light-emitting diode 112a of the second row are arranged in the top-and-bottom direction. In the example of FIG. 9B, each light-emitting diode 111a of the first row and each light-emitting diode 111a of the second row are obliquely arranged, and each light-emitting diode 112a of the first row and each light-emitting diode 112a of the second row are obliquely arranged. In the example of FIG. 9C, the plurality of light-emitting diodes 111a, 112a are arranged in four rows.

While the light-emitting diodes are used as each of the first light source 111 and the second light source 112 in the above-mentioned embodiment, another light-emitting devices such as laser diodes may be used as each of the first light source 111 and the second light source 112.

As a material for the metal support substrate 11, another metal or an alloy such as a 42 alloy, aluminum, copper-beryllium or phosphor bronze, or the like may be used instead of stainless. As a material for the base insulating layer 12, another synthetic resin such as polyamide imide, acryl, polyethersulfone, polyethylene terephthalate (PET), polyethylenenaphthalate, polyvinyl chloride, or epoxy may be used instead of polyimide.

As a material for the conductor traces 14, another metal such as gold (Au) or aluminum, or an alloy such as a copper alloy or an aluminum alloy may be used instead of copper. As a material for the metal cover layer 15, another metal such as tin or an alloy may be used instead of nickel.

As a material for the cover insulating layer 16, another synthetic resin such as polyamide imide, acryl, polyethersulfone, polyethylene terephthalate (PET), polyethylenenaphthalate, polyvinyl chloride, or epoxy may be used instead of polyimide.

The printed circuit board being a subject of the inspection is not limited to a suspension board having a circuit and may be another printed circuit board such as a flexible printed circuit board or a COF (Chip on Film) substrate.

While preferred embodiments of the present invention have been described above, it is to be understood that variations and modifications will be apparent to those skilled in the art without departing the scope and spirit of the present invention. The scope of the present invention, therefore, is to be determined solely by the following claims.

INDUSTRIAL APPLICABILITY

The present invention can be utilized for manufacturing, inspecting or the like of printed circuit boards.

I claim:

1. A method of manufacturing a printed circuit board including the steps of:
fabricating a first printed circuit board and a second printed circuit board that each include a metal support substrate, a first insulating layer positioned over the metal support substrate, a wiring trace positioned over the first insulating layer and a second insulating layer positioned over the wiring trace; and
performing inspection of the first printed circuit board and the second printed circuit board, wherein
the step of fabricating the first printed circuit board and the second printed circuit board includes fabricating the first printed circuit board in which the first and second insulating layers are formed of a first insulating material, and fabricating the second printed circuit board in which the first and second insulating layers are formed of a second insulating material different from the first insulating material,
the step of performing the inspection includes
irradiating the first printed circuit board with first light having a peak wavelength in a first wavelength region during inspection of the first printed circuit board, and irradiating the second printed circuit board with second light having a peak wavelength in a second wavelength region different from the first wavelength region during inspection of the second printed circuit board,
producing an image of the first printed circuit board based on reflected light from the first printed circuit board during the inspection of the first printed circuit board, and producing an image of the second printed circuit board based on reflected light from the second printed circuit board during the inspection of the second printed circuit board, and
determining whether the wiring trace of the first printed circuit board is defective based on the image of the first printed circuit board during the inspection of the first printed circuit board, and determining whether the wiring trace of the second printed circuit board is defective based on the image of the second printed circuit board during the inspection of the second printed circuit board,
wherein a ratio of light reflected by the wiring trace and emitted from the first or second printed circuit board to light incident on the first or second printed circuit board respectively is defined as wiring reflectance, and a ratio of light reflected by the metal support substrate and emitted from the first or second printed circuit board to light incident on the first or second printed circuit board respectively is defined as substrate reflectance, wherein the first printed circuit board has characteristics in which a difference between the wiring reflectance of the first printed circuit board and the substrate reflectance of the first printed circuit board regarding the first light is larger than a difference between the wiring reflectance of the second printed circuit board and the substrate reflectance of the second printed circuit board regarding the second light, and wherein the second printed circuit board has characteristics in which a difference between the wiring reflectance of the second printed circuit board and the substrate reflectance of the second printed circuit board regarding the second light is larger than a difference between the wiring reflectance of the first printed circuit board and the substrate reflectance of the first printed circuit board regarding the first light.

2. The method of manufacturing the printed circuit board according to claim 1, wherein
the first wavelength region is not less than 425 nm and not more than 525 nm, and the second wavelength region is not less than 630 nm and not more than 850 nm.

3. The method of manufacturing the printed circuit board according to claim 2, wherein
the first printed circuit board is irradiated with the first light by a first light-emitting device that generates violet light or blue light, and the second printed circuit board is irradiated with the second light by a second light-emitting device that generates red light or infrared light.

4. The method of manufacturing the printed circuit board according to claim 2, wherein
the first insulating material has a light transmittance higher than that of the second insulating layer at each wavelength in a range of not less than 425 nm and not more than 850 nm.

5. The method of manufacturing the printed circuit board according to claim 4, wherein
the light transmittances of the first and second insulating materials increase as wavelengths of light increase in the range of not less than 425 nm and not more than 850 nm.

6. A method of inspecting a first printed circuit board and a second printed circuit board that each include a metal support substrate, a first insulating layer positioned over the metal support substrate, a wiring trace positioned over the first insulating layer and a second insulating layer positioned over the wiring trace, wherein
the first and second insulating layers of the first printed circuit board are formed of a first insulating material and the first and second insulating layers of the second printed circuit board are formed of a second insulating material, the method of inspecting the printed circuit board includes the steps of
irradiating the first printed circuit board with first light having a peak wavelength in a first wavelength region during inspection of the first printed circuit board, and irradiating the second printed circuit board with second light having a peak wavelength in a second wavelength region different from the first wavelength region during inspection of the second printed circuit board, producing an image of the first printed circuit board based on reflected light from the first printed circuit board during the inspection of the first printed circuit board, and producing an image of the second printed circuit board based on reflected light from the second printed circuit board during the inspection of the second printed circuit board, and determining whether the wiring trace of the first printed circuit board is defective based on the image of the first printed circuit board during the inspection of the first printed circuit board, and determining whether the wiring trace of the second printed circuit board is defective based on the image of the second printed circuit board during the inspection of the second printed circuit board, wherein a ratio of light reflected by the wiring trace and emitted from the first or second printed circuit board to light incident on the first or second printed circuit board respectively is defined as wiring reflectance, and a ratio of light reflected by the metal support substrate and emitted from the first or second printed circuit board to light incident on the first or second printed circuit board respectively is defined as substrate reflectance, wherein the first printed circuit board has characteristics in which a difference between the wiring reflectance of the first printed circuit board and the substrate reflectance of the first printed circuit board regarding the first light is larger than a difference between the wiring reflectance of the second printed circuit board and the substrate reflectance of the second printed circuit board regarding the second light, and wherein the second printed circuit board has characteristics in which a difference between the wiring reflectance of the second printed circuit board and the substrate reflectance of the second printed circuit board regarding the second light is larger than a difference between the wiring reflectance of the first printed circuit board and the substrate reflectance of the first printed circuit board regarding the first light.

* * * * *